United States Patent [19]

Barron et al.

[11] Patent Number: 4,844,252

[45] Date of Patent: Jul. 4, 1989

[54] MULTI-PART DISPOSABLE HANDLE FOR HOSPITAL SURGERY ROOM LIGHT FIXTURE

[75] Inventors: John M. Barron, Granda Hills, Calif.; Robert T. Horan, Tucson, Ariz.; Moshe M. Hoftman, Northridge, Calif.; William L. Noack, Camarillo, Calif.; Dan Sandel, Tarzana, Calif.

[73] Assignee: Devon Industries, Inc., Chatsworth, Calif.

[21] Appl. No.: 224,896

[22] Filed: Jul. 27, 1988

[51] Int. Cl.⁴ .............................................. B65D 69/00
[52] U.S. Cl. .................................. 206/223; 206/438; 16/111 R; 362/804
[58] Field of Search ..................... 206/223, 438, 439; 220/85 E, 85 D, 90.4, 94; 16/111 R; 362/269, 285, 804; 215/100.5

[56] References Cited

U.S. PATENT DOCUMENTS

| | | | |
|---|---|---|---|
| 2,920,804 | 1/1960 | Minton | 215/100.5 |
| 3,341,062 | 9/1967 | Phillips | 220/90.4 |
| 4,135,231 | 1/1979 | Fisher | 362/285 |
| 4,307,439 | 12/1981 | Sassmannshausen | 362/285 |
| 4,402,407 | 9/1983 | Maly | 206/438 |
| 4,408,692 | 10/1983 | Sigel et al. | 206/438 |
| 4,538,214 | 8/1985 | Fisher et al. | 362/285 |
| 4,559,671 | 12/1985 | Andrews et al. | 362/804 |
| 4,605,124 | 8/1986 | Sandel . | |

OTHER PUBLICATIONS

SYBRON "Clinical Technology Steri-Grip Disposable Light Handle System" (known to applicants before applicants' date of invention).
U.S. Ser. No. 765,657 dated 8/1985 by Jefferson.

Primary Examiner—David T. Fidei
Attorney, Agent, or Firm—Poms, Smith, Lande & Rose

[57] ABSTRACT

A sterilizable multi-part handle for attachment to a handle receiving fitting of a hospital surgery room light fixture is made of light weight, inexpensive molded plastic parts which are disposable after use, the handle including a handle body having a body grip portion and a threaded head portion to engage the fixture fitting and a disc separate from the handle which is provided with a central aperture via which the disc is assembled to the handle in a snap on fit connection between the handle body and disc. The exemplary connecting means includes a plurality of detents provided on the inner periphery of the disc aperture which snap into and seat within a disc receiving groove provided in the handle body head portion adjacent a disc seating flange against which the disc seats when the handle is turned into tight engagement with the associated light fixture fitting. A sterilized kit of handle parts is disclosed wherein a pair of nested handle bodies seat in side by side relation upon a pair of stacked disc with a retainer strap thereabout to hold the array in such preassembled compact relation within a sterilized peel back type package.

17 Claims, 3 Drawing Sheets

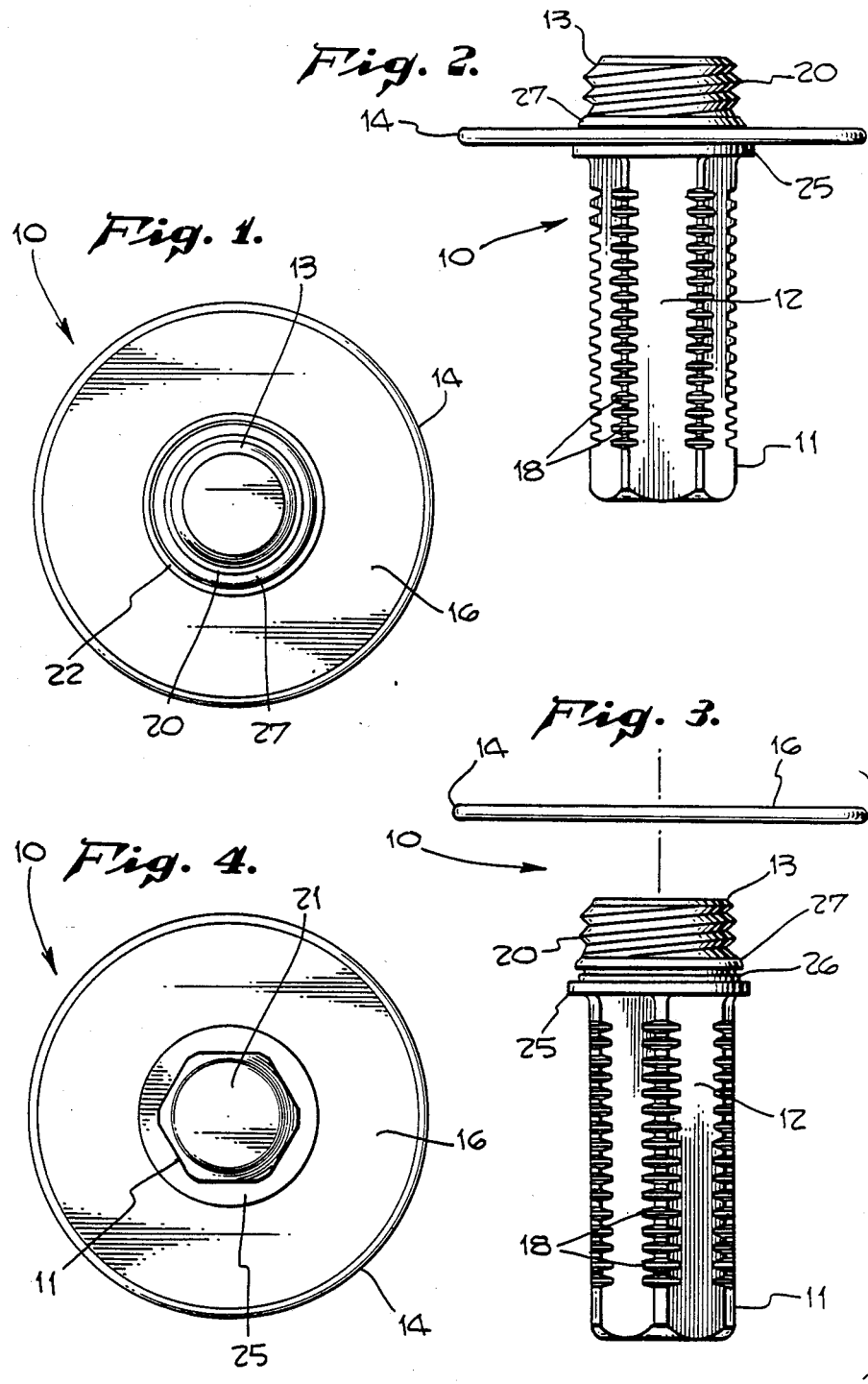

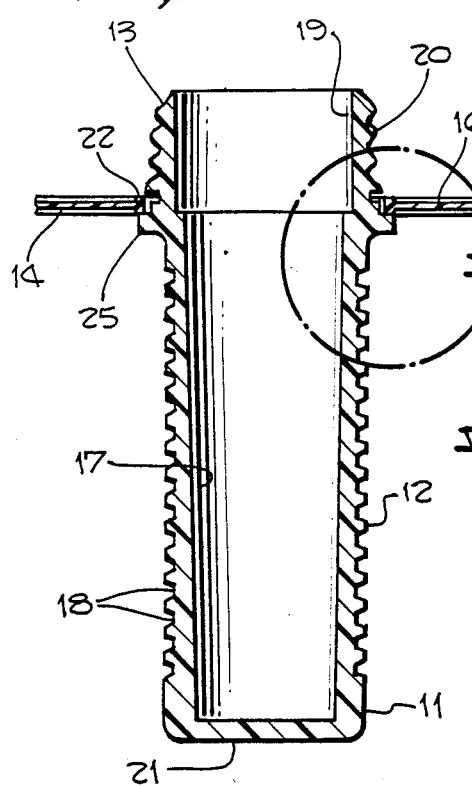
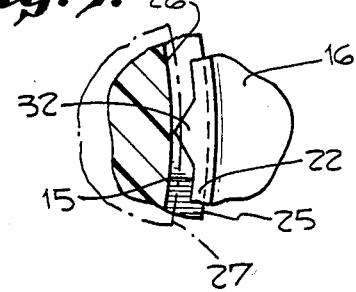
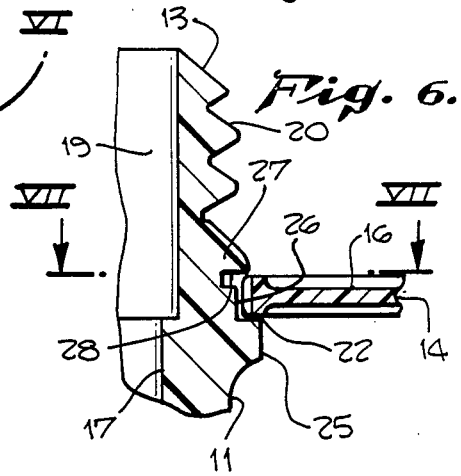
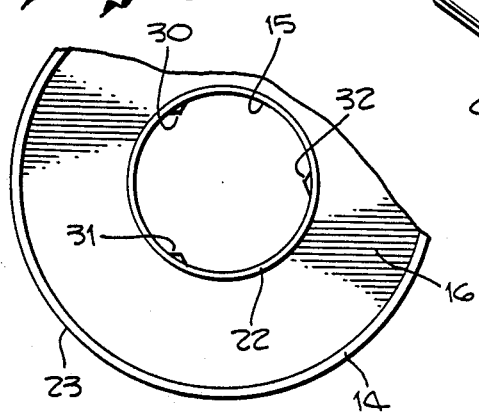
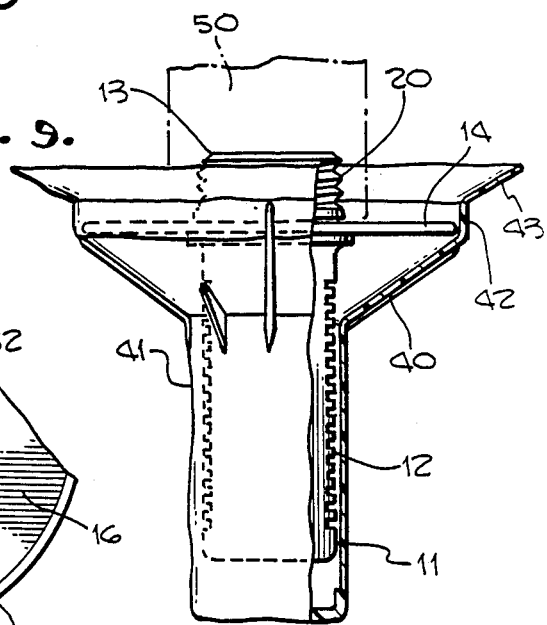

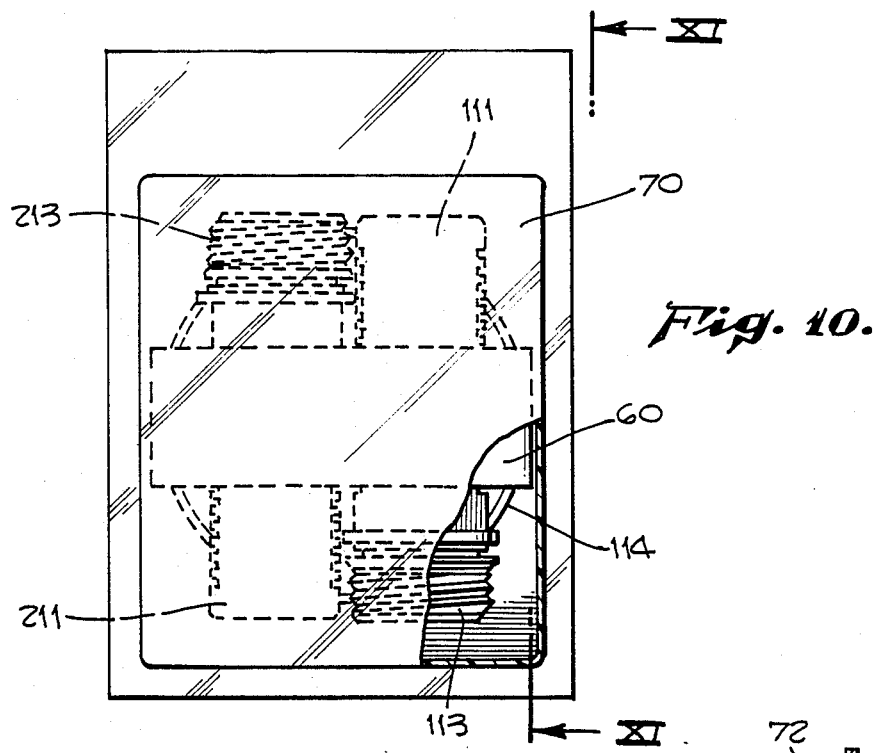
Fig. 10.
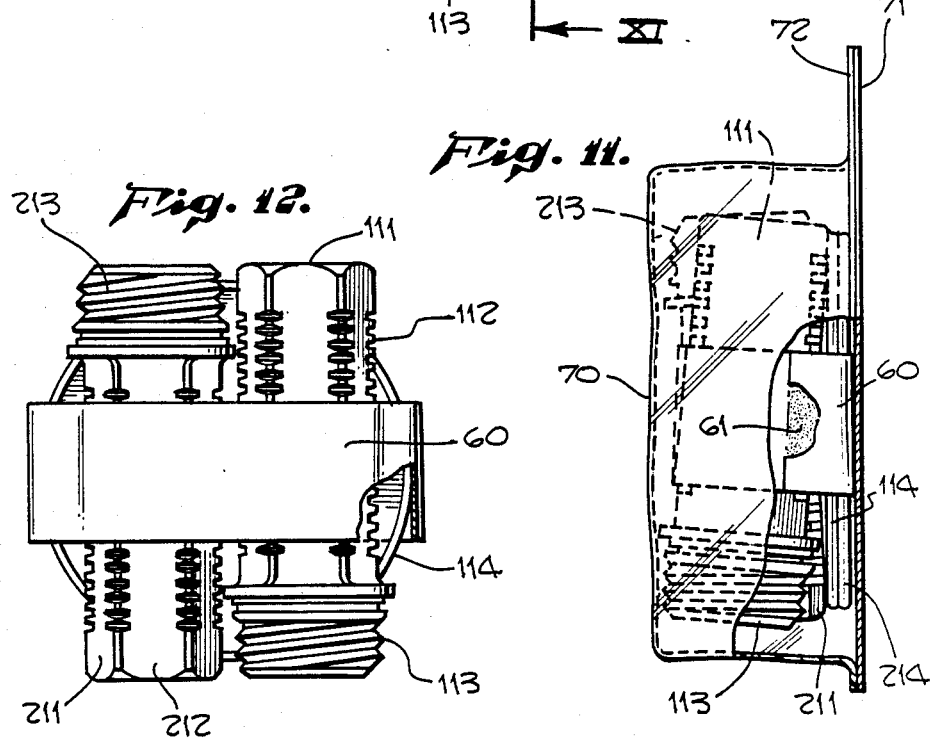
Fig. 11.
Fig. 12.

MULTI-PART DISPOSABLE HANDLE FOR HOSPITAL SURGERY ROOM LIGHT FIXTURE

BACKGROUND OF THE INVENTION

Generally stated, the present invention relates to disposable handles employed in the sterile zone or region above a hospital room surgery table which includes surgery lighting fixtures whose position relative the patient is adjusted by the surgeon engaging a sterile handle associated with the light fixture. More particularly, the present invention relates to a multi-part disposable handle of sterilizable plastic material which may be secured to the surgery light fixture within the sterile zone above the operating table by an operating room nurse or doctor together with a kit of such handle parts provided within a sterile container.

It is currently common practice to provide sterile handles and sterile coverings for handles for operating room light fixtures which are manipulated by the surgeon or operating room nurse during surgery on a hospital patient. It has been common heretofore to provide both permanent and disposable light handles and covers for such light fixtures as disclosed by way of example in prior U.S. Pat. No. 4,605,124. In that patent, a universal handle is provided for attachment to a lighting fixture associated adaptor fitting and a sterile, disposable thin walled impervious plastics or rubber like material cover is provided over the hollow grip and integral flange portions of the handle. While the cover is foldable into a compact shape for packaging as disclosed in said patent, the adaptor handle is not. In a commercial embodiment of the universal handle of said patent, a metal flange is assembled to a metal grip which provides for a bulky potentially stress inducing configuration for packaging within sterile packages of the thin walled peel back type employed in medical environments for dispensing sterile objects contained therein. It has therefore come to our attention that it would be desirable to provide a disposable handle construction, which may be used with or without a sterile cover of the type disclosed in said '124 patent, which would facilitate the packaging, shipping and dispensing of the same from typical sterilizable medical peel back type packages. It would also be desirable to provide such a handle construction which would be made of light weight inexpensive plastic materials suitable for disposable after a single sterile use, if desired, and which was provided in such a manner that it would be easy for the operating room nurse or doctor to manipulate the handle while in sterile condition for assembly to a typical operating room lighting fixture.

SUMMARY OF THE INVENTION

With the foregoing in mind, it is the primary object of the present invention to disclose and provide a sterilizable multi-part handle for attachment to a surgery room light fixture handle fitting, or handle adaptor fitting, which is easy to package in multiple numbers in a sterilized package, is inexpensive to manufacture, easy to dispense and assemble for use with a light fixture and facilitates the maintenance of the desired sterile condition of the sterile zone above the operating table to and including the location of the light fixture adjusting handles.

Generally stated, the present invention in such sterilizable multi-part handle includes the provision of a handle body having a body grip portion and head portion to engage with the light fixture associated fitting and a disc, separate from said handle, which is mounted to the handle by a central aperture provided within the disc, the handle body providing the sterile handle for gripping by the operating room nurse or doctor and the disc providing a sterile barrier preventing engagement of the fingers of the nurse or doctor with unsterilized adjacent portions of the light fixture itself. Connecting means are associated with the handle body and such disc in accordance with the present invention to facilitate a preassembly mounting of the disc to the handle preparatory to when the handle is secured to the light fixture, such securement of the handle to the fixture trapping the associated disc between the fixture and handle body.

More specifically, the handle body in accordance with present invention is provided in the form of a molded, one-piece sterilizable plastics material tubular body including a body grip portion having a roughened or scored exterior surface to improve the grip characteristics thereof as well as a head portion in the form of a hollow boss having an exterior pipe type thread to facilitate the reception thereof into a mating internally threaded adaptor provided on the light fixture. The disc is provided in the form of a molded, one piece, sterilizable, plastics material disc having inner and outer peripheral circular beads formed integrally of a connecting annular web portion, the disc and grip portion of the handle being provided to fit within a sterile cover provided in accordance with the disclosure of U.S. Pat. No. 4,605,124.

Exemplary connecting means in accordance with the present invention include the provision of a disc receiving groove in the handle head portion formed between an annular abutment, over which the centrally apertured disc is pressed fit, and adjacent to a disc seating flange against which the disc is seated when the handle is turned down upon the associate light fixture adaptor fitting. A plurality of detents are provided on the interior surface of the central aperture of the disc to cooperate with the annular abutment and disc receiving groove to provide a snap on assembly of the disc to the handle body to facilitate positioning of the two loosely assembled parts relative the light fixture adapter fitting, turning the handle body down on to the light fixture fitting securing the disc between the fixture fitting and handle body associated disc seating flange.

A sterilizable packaged kit of such easily assembled multi-part light weight plastic molded handle parts is provided by stacking to such discs, one upon the other in a vertically stacked relation and seating a pair of handle bodies in side by side relation upon the upper one of the stacked discs. A retainer strap may be wound about the handle bodies and discs to hold them in a compact array thereof within a peel back type of sterilizable package for storage and shipment to a location of use. The operating room nurse or doctor may simply peel back portions of the sterile package of the kit thus provided and deposit a pair of handle bodies and discs on a sterilized table top, remove the retainer strap and assemble one or both of such handles for easy attachment to the over head light fixture. If a first one of the handles becomes contaminated, a second one of the packaged handles may be employed and/or a sterile cover may be employed to over come any none sterile conditions affecting the handles as may occur in typical operating room situations.

It is submitted that those skilled in the art will obtain a better understanding of the construction and mode of operation of the present invention in a sterilizable multi-part handle and handle kit for attachment to a hospital room lighting fixture, in accordance with the present invention, as well as become aware of additional advantages and objects thereof from a consideration of the following detailed description of the preferred exemplary embodiments of such handle and handle kit. Reference will be made to appended sheets of drawings which will be first described briefly.

BRIEF DESCRIPTION OF THE DRAWINGS

FIG. 1 is a top view of an exemplary embodiment of sterilizable multi-part plastics material handle for attachment to a handle receiving fitting on a medical surgery room light fixture in accordance with the present invention.

FIG. 2 is a side, elevational view of the multi-part handle of FIG. 1.

FIG. 3 is a view as in FIG. 2 with the multi-part handle shown in preassembled relationship.

FIG. 4 is a bottom view of the handle of FIGS. 1 through 3.

FIG. 5 is a vertical section view of the exemplary embodiment of multi-part handle of FIGS. 1 through 4 in accordance with the present invention.

FIG. 6 is a detail section view of a portion of the handle of FIG. 5 taken therein in the region of VI—VI.

FIG. 7 is a further detail view, partially in section, of the exemplary handle taken along the plane VII—VII in FIG. 6.

FIG. 8 is a plan view of a preferred exemplary embodiment of the disc employed in the handle of FIGS. 1 through 7.

FIG. 9 is a side elevational view, partially in section, of the exemplary embodiment of handle of FIGS. 1 through 8 with a disposable thin walled plastics material cover assembled thereto.

FIG. 10 is a plan view of a preferred exemplary embodiment of a sterilized, packaged kit of a pair of the exemplary multi-part handles of FIGS. 1 through 9.

FIG. 11 is a side view, partially in section, of the kit of FIG. 10 taken therein along the plan X—X.

FIG. 12 is a plan view of the kit of FIGS. 10 and 11 after removal of the array of handle grips and discs within a surrounding retention strap have been removed from the sterile package of FIGS. 10 and 11.

DETAILED DESCRIPTION OF THE PREFERRED EXEMPLARY EMBODIMENTS

Referring now initially to FIGS. 1 through 4, a preferred exemplary embodiment of sterilizable multi-part handle for attachment to a handle receiving fitting on a medical surgery room light fixture is illustrated generally at 10. As seen in FIG. 3, the multi-part handle, in accordance with the present invention is provided as a two part assembly of a handle body 11, having a body grip portion 12 and a head portion 13 to engage with a mating light fixture associated fitting, and a disc 14 provided separate of the handle body 11 which has a central aperture 15, as best seen in FIG. 8, within a surrounding annular web 16. The handle body 11, in accordance with the present invention, is provided in the form of a molded one piece sterilizable plastics material (such material being well known in the industry) tubular body having an inner bore 17 as seen in FIG. 5. The body grip portion 12 is preferably scored, as by the cut outs 18 to enhance the grip characteristics thereof. Other forms of scoring or roughening of the grip portion 12 may be employed within the scope of the present invention to provide an improved grip of the handle body. As is also seen in FIG. 5, the head portion 13 of the exemplary embodiment of multi-part handle of the present invention is provided in the form of a hollow boss having an interior bore 19 and an exterior pipe type thread 20. It is customary to provide adapter fittings for the light fixtures of hospital surgery room facilities to accommodate the fastening of the disposable handle thereto. In accordance with the handle of the present invention, an appropriate mating adapter fitting is provided for attachment to the light fixture handle mount which has an appropriate female thread to accommodate the easily assembled pipe type thread as illustrated in the present exemplary embodiment. Also as seen in FIGS. 4 and 5, the lower end 21 of the handle body 11 is closed as is typical of light fixture handles for surgery room light fixtures. Further, while the exemplary handle of FIGS. 1 through 5 is shown as being of sixth sided polygon cross section to facilitate the grip aspects thereof, other shapes of handle body 11 may be employed.

Referring now to FIGS. 2 and 8, the disc 14 of the handle of the present invention is provided as a separately molded one-piece sterilizable plastics material disc having the central aperture 15. An inner bead 22 surrounds aperture 15 while a peripheral bead 23 surrounds the relatively thinner web 16 which is of annular configuration extending between the inner bead 22 and outer bead 23.

Connecting means are associated with the handle body 11, and particularly its head portion 13, and the disc 14, particular the disc aperture 15, for mounting the disc 14 to the handle body 11 prior to connecting the handle to the surgery room light fixture. In the preferred exemplary embodiment, such connecting means includes the provision of an annular seating flange 25 on the handle body head portion 13 as best seen in FIGS. 3, 5 and 6. Seating flange 25 is formed integrally of handle body 11 in the head portion 13 below the threads 20 and generally adjacent the body grip portion 12. The outer diameter of flange 25 is larger than the outer diameter of the largest thread of threads 20 so as to receive disc 14 thereon, as seen in FIGS. 5 and 6, the aperture 15 of disc 14 being sufficiently large to pass over head portion 13 but not large enough to pass flange 25 on assembly thereof to the handle body 11. A disc receiving groove 26, as seen in FIGS. 5 and 6, is provided in the head portion 13 between the annular protuberance 27 and seating flange 25.

As is also particularly contemplated within the present invention, the exemplary connecting means includes the provision of a plurality of detents, as the triangular detents 30, 31, and 32 as seen in FIG. 8, on the inner surface of aperture 15, such detents preferably being formed integrally thereof. As best seen in FIG. 6, opposite end portions of each of the detents 30, 31 and 32 are rounded or chamfered in directions facing laterally of the disc 14 to facilitate a snap on fit of disc 14 over protuberance 27 and into an assembled relation with handle body 11 by virtue of the retention of the detents 30, 31 and 32 within groove 26 by the adjacent annular protuberance 27 and seating flange 25. In order to improve the resiliency aspects of protuberance 27, a relief groove 28 is preferably provided adjacent protuberance 27, as seen in FIG. 6, to facilitate the snap on fit of the disc 14 over the protuberance 27 as seen in FIGS. 5–7.

While it is contemplated within the present invention that the two part handle of the present invention will be provided in a sterile condition to the operating room nurse or doctor who is to affix it to the surgery room light fixture adapter fitting, it is possible that on occasion it may become desirable to employ a sterile cover to assure the sterility of the installed handle for the light fixture. In such instances, a disposable thin walled plastics material cover 40 may be applied thereto as seen in FIG. 9. Cover 40 may be constructed in accordance with the disclosure of prior U.S. Pat. No. 4,605,124, the disclosure of which is incorporated herewith by reference. For purposes of the present discussion, it may be noted that the handle body 11 is provided so as to fit within the grip portion 41 of cover 40 while the outer diameter of disc 14 is provided to fit snugly within the upstanding wall 42 adjacent top flange 43. As described in said patent, the top wall 42 of cover 40 is provided so as to provide a somewhat snap on type fit over an associate handle flange; disc 14 and its peripheral bead 23 of the handle of the present invention being sized to receive such cover 40 in a snap on tight fit as disclosed in said patent. As shown in dotted line in FIG. 9, a light fixture adapter 50 receives the threaded head portion 13 by turning threads 20 therein until the disc 14 abuts the underside of the fitting 50. The preassembly of disc 14 to handle 11 afforded by the exemplary embodiment of connecting means described hereinbefore thus facilitates the positioning of the multi-part handle in its assembled relation for turning of the handle into the fitting, the disc 14 and handle body 11 being thereafter held in tight assembled relation by the light fixture fitting 50 pressing disc 14 down on the seating flange 25.

As is also particularly contemplated within the present invention, the multi-part handle of the present invention facilitates the packaging thereof in a sterilized packaged kit of easily assembled handle parts as seen in FIGS. 10, 11 and 12. A pair of discs, constructed as disc 14 of FIGS. 1 through 9, are preferably provided in a stacked relation one on top of the other as illustrated by the exemplary discs 114 and 214 in FIGS. 10 through 12. A pair of handle bodies 111 and 211, constructed as handle body 11 of FIGS. 1 through 9, are preferably provided in side by side relation resting upon the upper disc 114 of the stacked pair of discs. Preferably such handle bodies 111 and 112 are nested in such side by side relation with the head portions 113 and 213 lying adjacent the grip portion 112 and 212, respectively, of the other handle body as best seen in FIG. 12. By virtue of the larger diameter head portions on each of the handle bodies, the nesting of the handle bodies as illustrated in FIG. 12 provides for a more compact stable array of discs and handle bodies as illustrated.

A retainer strap 60, in accordance with the present invention, is wound about the stacked array of discs 114, 214 and handle bodies 111 and 211 to hold the same in an assembled array as seen in FIG. 12. Such retainer strap 60 preferably comprises a paper like strip which is easily assembled about the handle parts and with strip end thereof held to each other as by a simple pressure sensitive adhesive as indicated at 61 in FIG. 11. The strap 60 may therefore be either broken or unpeeled from its adhesive attachment to itself to facilitate release of the stacked array of handle parts.

As seen in FIGS. 10 and 11, a conventional sterile package 70 may be provided to enclose the sterilized handle parts and retainer strap within a sterile container, the latter including a backing sheet 71 with a vacuum formed or otherwise provided covering sheet 72 as known per se in the industry. Covering 72 may be peeled back off of backing 71 to facilitate the operating room nurse or doctor simply depositing the retained array of handle parts on a sterile table in the operating room. The operating room nurse or doctor may then simply remove the retainer strap 60 and assembly one or both of the handle sets of disc and handle body. Where the operating room lighting fixture has two handles, or there are two light fixtures, and the use of two handles is thus required, the provision of a pair of such handles by the kit of the present invention facilitates the availability thereof to the operating room or doctor in a sterile, easily manipulated condition.

Having thus described a preferred exemplary embodiment of multi-part handle for attachment to an operating room light fixture, in accordance with the present invention, as well as a preferred form of sterilized light handle part packaged kit thereof it should be now apparent to those skilled in the art that the affore stated objects and advantages of the present invention have been attained hereby and that various modifications, adaptations and alternative embodiments may be made within the spirit and scope of the present invention which is defined by the following claims.

We claim:

1. A sterilizable multi-part handle for attachment to a handle receiving fitting on a medical surgery room light fixture, said handle comprising:
   a handle body having a body grip portion and a head portion to engage said fitting;
   a disc separate from said handle and having a central aperture within a surrounding annular web; and
   connecting means associated with said handle body head portion and said disc aperture for mounting said disc to said handle body preparatory to mounting said handle to said light fixture.

2. The sterilizable multi-part handle of claim 1 wherein:
   said handle body is provided in the form of a molded one-piece sterilizable plastics material tubular body having a body grip portion having a scored exterior surface and said head portion is a hollow boss having an exterior pipe type thread.

3. The sterilizable multi-part handle of claim 2 wherein:
   said disc is provided in the form of a molded one piece sterilizable plastics material disc.

4. The sterilizable multi-part handle of claim 3 wherein:
   said body grip portion and disc are provided with an enveloping thin walled disposable plastic material cover.

5. The sterilizable multi-part handle of claim 4 wherein:
   said disc has a peripheral bead and said cover has an annular flange, said head fitting snugly within said flange.

6. The sterilizable multi-part handle of claim 1 wherein said connecting means comprises:
   a seating flange on said handle body head portion generally adjacent said body grip portion against which said disc seats when assembled thereto.

7. The sterilizable multi-part handle of claim 1 wherein said connecting means comprises:

a disc receiving groove in said head portion adjacent said seating flange which receives said disc partially therein when said disc is seated against said seating flange.

8. The sterilizable multi-part handle of claim 7 wherein said handle body head portion has an integral snap ring like annular protuberance portion adjacent said disc receiving groove over which said disc must pass to enter said disc receiving groove.

9. The sterilizable multi-part handle of claim 7 wherein said handle body head portion is provided with a relief groove between said annular protuberance portion and said disc receiving groove providing resiliency to said protuberance portion to facilitate said disc passing over the same into said disc receiving groove.

10. The sterilizable multi-part handle of claims 7, 8 or 9 wherein said disc is provided with a plurality of detents protruding inwardly of said central aperture to snap over said adjacent portions of said head portion as said disc is seated against said seating flange.

11. The sterilizable multi-part handle of claim 1 wherein said connecting means comprises:
a annular protuberance about said handle body head portion having an outer diameter smaller than the inner diameter of said disc central aperture; and
one or more detents protruding inwardly of said central aperture on said disc to provide an interference snap on fit of said disc to said handle body when said disc aperture is forced over said annular protuberance.

12. The sterilizable multi-part handle of claim 11 wherein said one or more detents have chamfered end surfaces facing laterally of said disc to facilitate said snap on fit of said disc to said handle body.

13. A sterilized package kit of easily assembled multi-part light weight plastic molded handles for use with a medical surgery room light fixture having a handle receiving fitting, said kit being provided within a sterile package and comprising:
a pair of discs in stacked relation, one on top of the other;
a pair of handle bodies in side by side relation and resting on said one of said discs; and
a retainer strap wound about and holding said handle bodies and discs in a compact array thereof prior to their removal from said package and assembly of said discs to said handle bodies to provide assembled handles.

14. The kit of claim 13 wherein:
said pair of handle bodies each have a grip portion of generally uniform outer dimensions and a head portion of larger outer dimensions than said grip portions; and
said handle bodies are nested in side by side relation with the head portions of each of said bodies lying adjacent the grip portion of the other.

15. The kit of claim 13 wherein:
said retainer strap comprises an easily frangible paper like material.

16. The kit of claim 13 wherein said pair of discs are provided in the form of two individually molded, one piece circular and centrally apertured sterilizable plastic material discs.

17. The kit of claim 16 wherein said pair of handle bodies are provided in the form of two individually molded, one piece hollow sterilizable plastic material bodies having threaded head portions and externally scored body grip portions.

* * * * *

REEXAMINATION CERTIFICATE (1948th)
United States Patent [19]
Barron et al.

[11] B1 4,844,252
[45] Certificate Issued Mar. 16, 1993

[54] MULTI-PART DISPOSABLE HANDLE FOR HOSPITAL SURGERY ROOM LIGHT FIXTURE

[75] Inventors: John M. Barron, Granda Hills, Calif.; Robert T. Horan, Tucson, Ariz.; Moshe M. Hoftman, Northridge, Calif.; William L. Noack, Camarillo, Calif.; Dan Sandel, Tarzana, Calif.

[73] Assignee: Devon Industries, Inc., Chatsworth, Calif.

Reexamination Request:
No. 90/002,432, Sep. 12, 1991

Reexamination Certificate for:
Patent No.: 4,844,252
Issued: Jul. 4, 1989
Appl. No.: 224,896
Filed: Jul. 27, 1988

[51] Int. Cl.⁵ ............................................. B65D 69/00
[52] U.S. Cl. ..................... 206/223; 206/438; 16/111 R; 362/804
[58] Field of Search ............ 362/109; 116/114 R, 116/114 A, DIG. 24; 604/192, 263

[56] References Cited

U.S. PATENT DOCUMENTS

| | | | |
|---|---|---|---|
| D. 289,206 | 4/1987 | Scoville et al. | D26/113 |
| 3,761,013 | 9/1973 | Schuster | 206/439 |
| 3,991,881 | 11/1976 | Augurt | 206/439 |
| 4,316,237 | 2/1982 | Yamada et al. | 362/33 |
| 4,559,042 | 12/1985 | Votel | 604/192 |
| 4,742,910 | 11/1988 | Staebler | 604/192 |
| 4,900,309 | 2/1990 | Netherton et al. | 604/192 |
| 4,919,656 | 4/1990 | Bracker et al. | 604/263 |

FOREIGN PATENT DOCUMENTS 122643 9/1948 Sweden ............ 240/41.15

*Primary Examiner*—David T. Fidei
*Attorney, Agent, or Firm*—Poms, Smith, Lande & Rose

[57] ABSTRACT

A sterilizable multi-part handle for attachment to a handle receiving fitting of a hospital surgery room light fixture is made of light weight, inexpensive molded plastic parts which are disposable after use, the handle including a handle body having a body grip portion and a threaded head portion to engage the fixture fitting and a disc separate from the handle which is provided with a central aperture via which the disc is assembled to the handle in a snap on fit connection between the handle body and disc. The exemplary connecting means includes a plurality of detents provided on the inner periphery of the disc aperture which snap into and seat within a disc receiving groove provided in the handle body head portion adjacent a disc seating flange against which the disc seats when the handle is turned into tight engagement with the associated light fixture fitting. A sterilized kit of handle parts is disclosed wherein a pair of nested handle bodies seat in side by side relation upon a pair of stacked disc with a retainer strap thereabout to hold the array in such preassembled compact relation within a sterilized peel back type package.

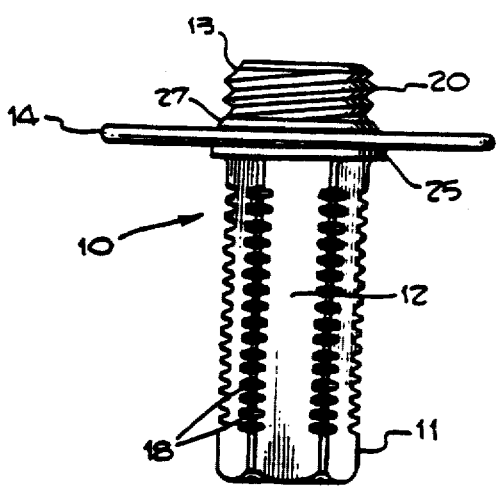

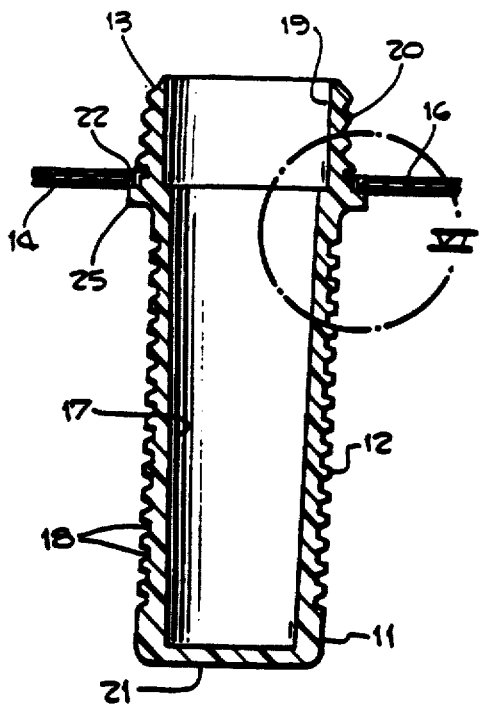

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 13, 14, 15, 16 and 17 is confirmed.

Claim 8 is cancelled.

Claims 1, 2, 5, 6, 7, 9, 10 and 11 are determined to be patentable as amended.

Claims 3, 4, and 12, dependent on an amended claim, are determined to be patentable.

1. A sterilizable multi-part handle for attachment to a handle receiving fitting on a medical surgery room light fixture, said handle comprising:
   a handle body having a body grip portion and a head portion to engage said fitting, *said head portion having an annular protuberance;*
   a disc separate from said handle and having a central aperture within a surrounding annular web, *said annular protuberance having a diameter less than the inner diameter of said central aperture*; and
   [connecting means associated with said handle body head portion and said disc aperture for mounting said disc to said handle body preparatory to mounting said handle to said light fixture] *at least one detent protruding inwardly of said central aperture that is forced over the annular protuberance to provide a snap-on fit connection between said handle body and said disc.*

2. The sterilizable multi-part handle of claim 1 wherein:
   said handle body is provided in the form of a molded one-piece sterilizable plastics material tubular body [having a], *said* body grip portion having a scored exterior surface and said head portion is a hollow boss having an exterior pipe type thread.

5. The sterilizable multi-part handle of claim 4 wherein:
   said disc has a peripheral bead and said cover has an annular flange, said [head] *bead* fitting snugly within said flange.

6. The sterilizable multi-part handle of claim 1 [wherein said connecting means comprises] *further comprising:*
   a seating flange on said handle body head portion generally adjacent said body grip portion against which said disc seats when assembled thereto.

7. The sterilizable multi-part handle of claim 1 [wherein said connecting means comprises] *further comprising:*
   a disc receiving groove in said head portion adjacent said seating flange which receives said disc partially therein when said disc is seated against said seating flange.

9. [The sterilizable multi-part handle of claim 7 wherein] *A sterilizable multi-part handle for attachment to a handle receiving fitting on a medical surgery room light fixture, said handle comprising:*
   *a handle body having a body grip portion and a head portion at an end of said handle body adjacent said fitting to engage said fitting;*
   *a disc separate from said handle and having a central aperture within a surrounding annular web; and*
   *connecting means associated with said handle body head portion and said disc aperture for mounting said disc to said handle body preparatory to mounting said handle to said light fixture, said connecting means providing a snap-on fit type connecting between said disc and said head portion after passing said head portion through said aperture, said connecting means comprises:*
   *a seating flange on said handle body head portion generally adjacent said body grip portion against which said disc seats when assembled thereto;*
   *a disc receiving groove in said head portion adjacent said seating flange which receives said disc partially therein when said disc is seated against said seating flange;*
   wherein said handle body head portion has an integral snap ring annular protuberance portion adjacent said disc receiving groove over which said disc must pass to enter said disc receiving groove, *and* said handle body head portion is provided with a relief groove between said annnular protuberance portion and said disc receiving groove providing resiliency to said protuberance portion to facilitate said disc passing over the same into said disc receiving groove.

10. The sterilizable multi-part handle of [claims 7, 8 or 9] *claim 9* wherein said disc is provided with a plurality of detents protruding inwardly of said central aperture to snap over said adjacent portions of said head portion as said disc is seated against said seating flange.

11. [The sterilizable multi-part handle of claim 1,] *A sterilizable multi-part handle for attachment to a handle receiving fitting on a medical surgery room light fixture, said handle comprising:*
    *a handle body having a body grip portion and a head portion at an end of said handle body adjacent said fitting to engage said fitting;*
    *a disc separate from said handle and having a central aperture within a surrounding annular web; and*
    *connecting means associated with said handle body head portion and said disc aperture for mounting said disc to said handle body preparatory to mounting said handle to said light fixture, said connecting means providing a snap-on fit type connection between said disc and said head portion after passing said head portion through said aperture;*
    wherein said connecting means comprises:
    a annular protuberance about said handle body head portion having an outer diameter smaller than the inner diameter of said disc central aperture; and
    one or more detents protruding inwardly of said central aperture on said disc to provide [an interference] *said snap on fit* of said disc to said handle body when said disc aperture is forced over said annular protuberance.

* * * * *